(12) United States Patent
Jiang et al.

(10) Patent No.: US 12,727,985 B2
(45) Date of Patent: Sep. 8, 2026

(54) SILICONE STENT, IMPLANTATION SYSTEM, AND MANUFACTURING METHOD

(71) Applicants: MICRO-TECH (NANJING) CO., LTD., Nanjing (CN); THE FIRST AFFILIATED HOSPITAL OF SOOCHOW UNIVERSITY, Suzhou (CN)

(72) Inventors: Junhong Jiang, Suzhou (CN); Changguo Wang, Suzhou (CN); Daxiong Zeng, Suzhou (CN); Derong Leng, Nanjing (CN); Jianyu Wei, Nanjing (CN); Zhenghua Shen, Nanjing (CN); Minghao Feng, Nanjing (CN)

(73) Assignees: MICRO-TECH (NANJING) CO., LTD., Nanjing (CN); THE FIRST AFFILIATED HOSPITAL OF SOOCHOW UNIVERSITY, Suzhou (CN)

( * ) Notice: Subject to any disclaimer, the term of this patent is extended or adjusted under 35 U.S.C. 154(b) by 824 days.

(21) Appl. No.: 18/015,390

(22) PCT Filed: Aug. 18, 2021

(86) PCT No.: PCT/CN2021/113300
§ 371 (c)(1),
(2) Date: Jan. 10, 2023

(87) PCT Pub. No.: WO2022/068453
PCT Pub. Date: Apr. 7, 2022

(65) Prior Publication Data

US 2023/0233314 A1 Jul. 27, 2023

(30) Foreign Application Priority Data

Sep. 30, 2020 (CN) ........................ 202011060507.8

(51) Int. Cl.
*A61F 2/04* (2013.01)
*A61F 2/91* (2013.01)
*A61F 2/966* (2013.01)

(52) U.S. Cl.
CPC .................. *A61F 2/04* (2013.01); *A61F 2/91* (2013.01); *A61F 2/966* (2013.01); *A61F 2002/046* (2013.01); *A61F 2240/001* (2013.01)

(58) Field of Classification Search
CPC .......... A61F 2002/046; A61F 2002/072; A61F 2/966
See application file for complete search history.

(56) References Cited

U.S. PATENT DOCUMENTS

2011/0295353 A1 12/2011 Harris et al.

FOREIGN PATENT DOCUMENTS

CA 2020957 C * 5/1996 ............ A61F 2/966
CN 1678366 A 10/2005
(Continued)

OTHER PUBLICATIONS

First Chinese Office Action for the corresponding Chinese Patent Application No. 2020110605078, mailed on Jun. 15, 2024, and its English translation, 20 pages.

*Primary Examiner* — Brian E Pellegrino
(74) *Attorney, Agent, or Firm* — Christian S. Hans; Bret E. Field; Bozicevic, Field & Francis LLP

(57) ABSTRACT

Provided are a silicone stent (100), an implantation system, and a manufacturing method. The silicone stent (100) includes a stent body (110). The stent body (110) includes a mesh frame (112) and a silicone body (111) molded on the mesh frame (112). A circumferentially sealed space (116) is defined within the silicone body (111). A distal end and a proximal end of the silicone body (111) respectively have a distal-end opening (115) and a proximal-end opening (114)
(Continued)

that communicate with the space (116). The mesh frame (112) circumferentially covers the silicone body (111), and runs in an axial direction of the silicone body (111). The mesh frame (112) extends from the proximal end of the silicone body (111) to the distal end of the silicone body (111).

7 Claims, 4 Drawing Sheets

(56) References Cited

FOREIGN PATENT DOCUMENTS

| | | | | |
|---|---|---|---|---|
| CN | 103874794 A | 6/2014 | | |
| CN | 204995617 U | 1/2016 | | |
| CN | 107115165 A | 9/2017 | | |
| CN | 208031341 U | 11/2018 | | |
| CN | 208081344 U | 11/2018 | | |
| CN | 109893314 A | 6/2019 | | |
| CN | 110251283 A | 9/2019 | | |
| CN | 111249044 A | 6/2020 | | |
| CN | 210990954 U | 7/2020 | | |
| CN | 211095014 U | 7/2020 | | |
| CN | 211433528 U | 9/2020 | | |
| CN | 112120838 A | 12/2020 | | |
| CN | 212234824 U | 12/2020 | | |
| EP | 2240215 B1 * | 1/2014 | ........... | A61L 31/125 |
| WO | WO-2009091899 A2 * | 7/2009 | ........... | A61L 31/125 |

* cited by examiner

SILICONE STENT, IMPLANTATION SYSTEM, AND MANUFACTURING METHOD

This application claims priority to Chinese Patent Application No. 2020110605078, filed with the China National Intellectual Property Administration on Sep. 30, 2020 and entitled "SILICONE STENT, IMPLANTATION SYSTEM, AND MANUFACTURING METHOD", which is incorporated herein by reference in its entirety.

FIELD OF THE INVENTION

This disclosure relates to the technical field of medical devices, and in particular, to a silicone stent, an implantation system, and a manufacturing method.

BACKGROUND OF THE INVENTION

An endotracheal stent is a support that is implanted in a trachea and has certain tension and elasticity. The endotracheal stent is implanted in the trachea to stretch the trachea, to ensure that the trachea is unobstructed. Existing endotracheal stents are classified into metal stents and non-metal stents. The non-metal stents are further classified into silicone stents and plastic stents. After long-term clinical research, it is found that long-term complications of the silicone stent, such as granulation hyperplasia and scar stenosis, are significantly fewer than those of the metal stent. Moreover, the silicone stent has advantages such as being easy to be removed after long-term implantation. Therefore, the silicone stent is recommended for a patient, with benign tracheal stenosis, that needs to be treated by using a stent.

However, while being released, the existing silicon stent needs to be placed in a particular pusher. A rigid bronchoscope is used in a case of general anesthesia. Releasing the silicon stent under blind visual according to a measurement method brings in difficulties in implantation, and thus surgery is much difficult. As a result, a learning curve of an implantation operation is long.

SUMMARY OF THE INVENTION

Objectives of this disclosure include, for example, providing a silicone stent that can improve the following technical problems in the prior art: the silicone stent is difficult to be implanted, surgery is much difficult, and a learning curve is long.

Objectives of this disclosure further include providing an implantation system that can improve the following technical problems in the prior art: the silicone stent is difficult to be implanted, surgery is much difficult, and a learning curve is long.

Objectives of this disclosure further include providing a manufacturing method that can manufacture the silicone stent described above. Therefore, the following technical problems in the prior art that the silicone stent is difficult to be implanted, surgery is much difficult, and that a learning curve is long can also be improved.

Embodiments of this disclosure can be implemented as follows.

An embodiment of this disclosure provides a silicone stent, including a stent body, wherein the stent body includes a mesh frame and a silicone body molded on the mesh frame; a circumferentially sealed space is defined within the silicone body; a distal end and a proximal end of the silicone body respectively have a distal-end opening and a proximal-end opening that communicate with the space; the mesh frame circumferentially covers the silicone body, and runs in an axial direction of the silicone body; and the mesh frame extends from the proximal end of the silicone body to the distal end of the silicone body.

In one or more embodiments, an outer peripheral wall of the stent body is provided with a plurality of protrusions in a protruding manner.

By providing a plurality of protrusions on the outer peripheral wall of the stent body in a protruding manner, abutting between the protrusion and a wall surface of a trachea can help to improve displacement of the silicone stent relative to the trachea during use. In other words, the protrusion can play a role in stabilizing a position of the stent in the trachea.

In one or more embodiments, the protrusion is integrally formed with the silicone body.

In one or more embodiments, the mesh frame has a protruding portion, and the protruding portion is film coated to form the protrusion.

In one or more embodiments, the protrusion is bonded and fixed on the stent body.

In one or more embodiments, the plurality of protrusions include a plurality columns of protrusions that are uniformly distributed along a circumferential direction of the stent body, and each column of protrusions include a plurality of protrusions disposed at intervals along an axial direction of the stent body.

In one or more embodiments, a plurality of protrusions in two adjacent columns of protrusions are alternately disposed along the axial direction of the stent body; or a plurality of protrusions in each column of protrusions are spirally distributed around an axis of the stent body; or a plurality of protrusions are distributed dispersedly.

By disposing protrusions on an outer peripheral wall of the stent body and setting the protrusion specifically, after the silicone stent is implanted into the human trachea, the protrusion abuts against the wall surface of the trachea, so that the wall surface of the trachea is separated from the outer peripheral wall of the stent body. A cilium on the wall surface of the trachea has certain space to swing. In this way, secretions around the silicone stent can be cleared by using the cilium. In other words, a mucus clearing function of the cilium is retained. Therefore, a use effect of the silicone stent becomes better.

In one or more embodiments, a thickness h of the protrusion (120) satisfies 0.5 mm≤h≤4 mm.

In one or more embodiments, a wall thickness d of the stent body satisfies 0.05 mm≤d≤0.8 mm.

In one or more embodiments, the silicone body is molded on the mesh frame by means of film coating.

The silicone body is molded on the mesh frame by means of film coating. In this way, a thickness of the silicone body, that is, the thickness of the stent body of the silicone stent, can be reduced more conveniently and simply, thereby further ensuring that the silicone stent can be placed in an implant. The silicone stent is implanted by using the implant in an Over Through Wire (OTW) manner.

In one or more embodiments, the mesh frame is braided by one metal wire.

In one or more embodiments, the silicone body is fixed at a periphery of the mesh frame.

In one or more embodiments, the stent body further includes skirt edges connected at two ends of the silicone body; and along an axial direction of the silicone stent, the skirt edges are located on two sides of the mesh frame.

In one or more embodiments, the skirt edge is integrally formed with the silicone body.

In one or more embodiments, the stent body further includes a silicone layer wrapping the mesh frame, and the silicone body is fixedly connected to the silicone layer.

An embodiment of this disclosure further provides an implantation system. The implantation system includes a delivery device and a silicone stent. The silicone stent includes a stent body, wherein the stent body includes a mesh frame and a silicone body molded on the mesh frame; a circumferentially sealed space is defined within the silicone body; a distal end and a proximal end of the silicone body respectively have a distal-end opening and a proximal-end opening that communicate with the space; the mesh frame circumferentially covers the silicone body, and runs in an axial direction of the silicone body; and the mesh frame extends from the proximal end of the silicone body to the distal end of the silicone body. The delivery device has an accommodation cavity, and the silicone stent is accommodated in the accommodation cavity in a contracted state, so that the silicone stent is implanted by the delivery device.

An embodiment of this disclosure further provides a manufacturing method for manufacturing a silicone stent. The manufacturing method includes:

molding a silicone body on a cylindrical mesh frame, so that a circumferentially sealed space is defined within the silicone body, wherein a distal end and a proximal end of the silicone body are respectively provided with a proximal-end opening and a distal-end opening that communicate with the space; the mesh frame circumferentially covers the silicone body, and runs in an axial direction of the silicone body; and the mesh frame extends from the proximal end of the silicone body to the distal end of the silicone body.

In one or more embodiments, the step of molding a silicone body on a cylindrical mesh frame includes: coating the mesh frame with silicone, to mold the silicone body on the mesh frame;

wherein the mesh frame has a protruding portion, and the protruding portion is film coated with silicone to form a protrusion of the silicone stent.

In one or more embodiments, the step of molding a silicone body on a cylindrical mesh frame includes: film coating the mesh frame with silicone, to mold the silicone body on the mesh frame, and obtain a stent body of the silicone stent; and after the step of molding a silicone body on a cylindrical mesh frame, the method includes: bonding a protrusion on an outer peripheral wall of the stent body, to obtain the silicone stent.

In one or more embodiments, the step of molding a silicone body on a cylindrical mesh frame includes: placing the mesh frame in a mold; and injecting liquid silicone into the mold, and filling a recess on an inner peripheral surface of the mold with the liquid silicone, so that after being cooled, the liquid silicone is wrapped on the mesh frame to form the silicone body, and an outer wall of the silicone body has a protrusion corresponding to the recess.

In one or more embodiments, the step of molding a silicone body on a cylindrical mesh frame includes:

respectively bonding and fixing a proximal end and a distal end of the mesh frame on an inner peripheral wall of a silicone cylinder, wherein a portion that is of the silicone cylinder and that is located between the proximal end and the distal end of the mesh frame forms the silicone body, and two ends in an axial direction of the silicone cylinder protrude out of the mesh frame to form skirt edges.

In one or more embodiments, the step of molding a silicone body on a cylindrical mesh frame includes:

sleeving a silicone cylinder on the mesh frame wrapped with a silicone layer; and vulcanizing the silicone cylinder and the mesh frame wrapped with the silicone layer, so that the silicone cylinder is bonded to the silicone layer, wherein a portion that is of the silicone cylinder and that is located between a proximal end and a distal end of the mesh frame forms the silicone body, and two ends in an axial direction of the silicone cylinder protrude out of the mesh frame to form skirt edges.

Beneficial effects of the silicone stent, the implantation system, and the manufacturing method in the embodiments of this disclosure include, for example:

The silicone stent provided in the embodiment of this disclosure includes the stent body.

The stent body includes the mesh frame and the silicone body molded on the mesh frame. The circumferentially sealed space is defined within the silicone body, and the distal end and the proximal end of the silicone body are respectively provided with the distal-end opening and the proximal-end opening that communicate with the space. During use, the silicone stent is implanted into the human trachea, and the space defined within the silicone body communicates with the trachea, thereby ensuring that the trachea is unobstructed. Because the stent body of the silicone stent is formed through the mesh frame and the silicone body together, and the mesh frame circumferentially covers the silicone body, along an axial direction, the mesh frame extends from the proximal end of the silicone body to the distal end of the silicone body. In this way, support force of the stent body can be effectively improved by the mesh frame. Compared with an existing silicone stent in which support force of a stent body is merely provided by a silicone body, the silicone stent provided in the embodiments can greatly reduce a wall thickness of the silicone body. Moreover, the wall thickness of the formed stent body is also greatly reduced. In this way, while being implanted, the silicone stent can be put into the implant, and can be implanted by using the implant under side view of a flexible bronchoscope in a conventional OTW manner. This is helpful to reduce difficulties in implantation and surgery, and thus a learning curve of an implantation operation can be effectively shortened.

The embodiments of this disclosure further provide an implantation system, including the delivery device and the silicone stent described above. According to the implantation system, the silicone stent can be implanted into the human trachea by the delivery device in the conventional OTW manner. Therefore, the implantation system has the following beneficial effects of the silicone stent: difficulties in implantation and surgery are low and the learning curve of the implantation operation is short.

The embodiments of this disclosure further provide a manufacturing method that can manufacture the silicone stent described above. Therefore, the manufactured silicone stent also has the beneficial effects of low difficulties in implantation and surgery and a short learning curve of the implantation operation.

BRIEF DESCRIPTION OF THE DRAWINGS

To more clearly describe the technical solutions of the embodiments of this disclosure, the accompanying drawings to be used in the embodiments are briefly illustrated below. It should be understood that the following accompanying drawings merely show some embodiments of this disclosure, and therefore should not be considered as a limitation to the scope. A person of ordinary skills in the art can also derive other related accompanying drawings according to these accompanying drawings without an effective effort.

LIST OF REFERENCE NUMERALS IN THE DRAWINGS

Figure 1:
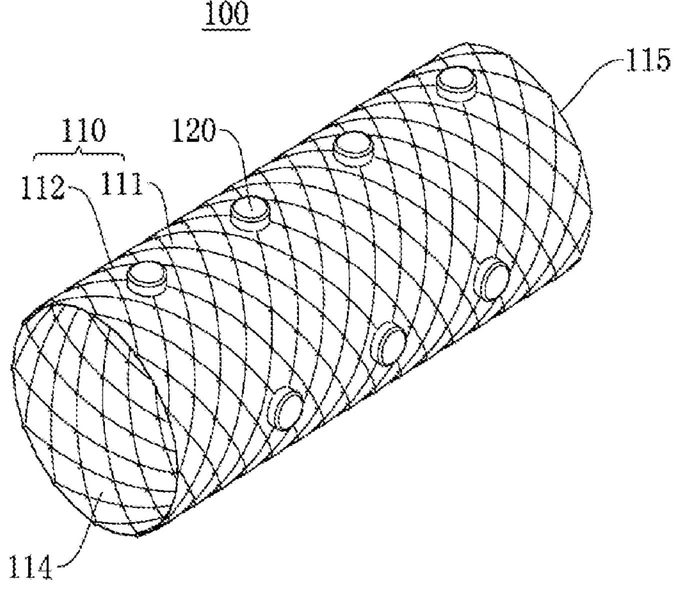
FIG. 1 is a schematic structural diagram of a silicone stent in a first visual angle according to an embodiment of this disclosure.

100 silicone stent
110 stent body
111 silicone body
112 mesh frame
113 outer peripheral wall
114 proximal-end opening
115 distal-end opening
116 space
117 metal wire
118 skirt edge
120 protrusion
121 first protrusion
122 second protrusion
200 delivery device
211 inner tube
212 middle tube
213 outer tube
214 accommodation cavity
215 developing ring
216 proximal-end handle
217 distal-end handle

DETAILED DESCRIPTION OF THE EMBODIMENTS

To make objectives, technical solutions, and advantages of the embodiments of this disclosure more clear, the technical solutions in the embodiments of this disclosure are clearly and completely described below in combination with the accompanying drawings in the embodiments of this disclosure. Apparently, the embodiments to be described are some and not all of the embodiments of this disclosure. Generally, components in the embodiments of this disclosure that are described and shown in the accompanying drawings herein can be arranged and designed in various configurations.

Therefore, the following detailed description of the embodiments of this disclosure that are provided in the accompanying drawings is not intended to limit the protection scope of this disclosure, but merely represents selected embodiments of this disclosure. According to the embodiments of this disclosure, all other embodiments derived, without an effective effort, by one of ordinary skills in the art fall within the protection scope of this disclosure.

It should be noted that, similar signs and letters in the following accompanying drawings indicate similar items. Therefore, once an item is defined in one of the accompanying drawings, there is no need to further define and explain the item in the subsequent accompanying drawings.

In the description of this disclosure, it should be noted that if there are orientations or positional relationships indicated by terms such as "up", "down", "inner", and "outer", the orientations or positional relationships are based on the accompanying drawings, or are orientations or positional relationships for which a product in this disclosure is usually placed during use, and are only for convenience of describing this disclosure and for simplifying operations, rather than being intended to indicate or imply that a device or an element referred to must have a particular orientation or be constructed and operated in a particular orientation.

Therefore, these should not be construed as limitation to this disclosure.

In addition, terms "first" and "second" are merely used for distinction in description, and cannot be understood as indicating or implying the relative importance.

It should be noted that features in the embodiments in this disclosure can be combined with each other if there is no conflict.

Figure 2:
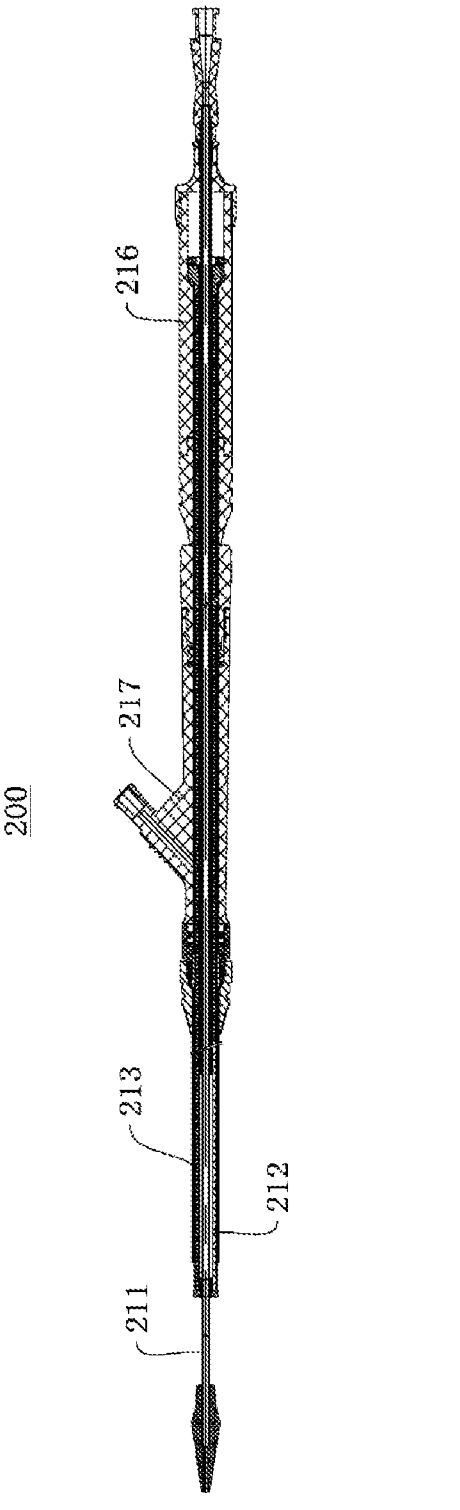
FIG. 2 is a schematic structural diagram of a delivery device according to an embodiment of this disclosure.
Figure 3:
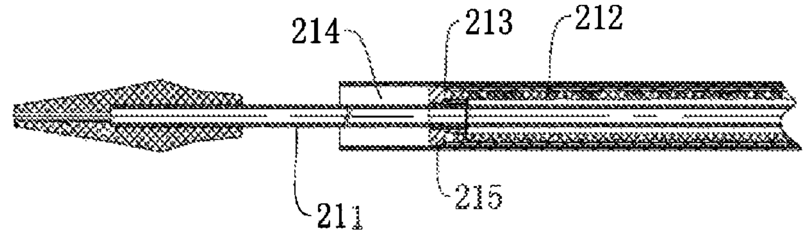
FIG. 3 is a schematic sectional view of a partial structure of a delivery device according to an embodiment of this disclosure.

FIG. 1 is a schematic structural diagram of a silicone stent 100 in a first visual angle according to an embodiment of this disclosure. FIG. 2 is a schematic structural diagram of a delivery device 200 according to an embodiment of this disclosure. FIG. 3 is a schematic sectional view of a partial structure of a delivery device 200 according to an embodiment of this disclosure. Referring to FIG. 1 to FIG. 3, an embodiment of this disclosure provides a silicone stent 100. Correspondingly, an implantation system (not shown in the figures) is provided.

The implantation system includes the silicone stent 100, and further includes a delivery device 200. The delivery device 200 has an accommodation space. While being implanted, the silicone stent 100 is accommodated in an accommodating cavity 214 in a contracted state, so that the silicone stent 100 is implanted by using the delivery device 200 under side view of a flexible bronchoscope in a conventional Over Through Wire (OTW for short hereinafter) manner. In other words, the delivery device 200 may be a delivery device 200 in a conventional OTW manner.

The silicone stent 100 includes a stent body 110. The stent body 110 includes a mesh frame 112 and a silicone body 111 molded on the mesh frame 112. The circumferentially sealed space 116 is defined within the silicone body 111, and a distal end and a proximal end of the silicone body 111 are respectively provided with a distal-end opening 115 and a proximal-end opening 114 that communicate with the space 116. During use, the silicone stent 100 is implanted into a human trachea, and the space 116 defined within the silicone body 111 enables two ends in the trachea at which the silicone stent 100 is placed to be communicated, thereby ensuring that the trachea is unobstructed. Because the stent body 110 of the silicone stent 100 is formed through the mesh frame 112 and the silicone body 111 together, and the mesh frame 112 circumferentially covers the silicone body 111, along an axial direction of the stent body 110, the mesh frame 112 extends from the proximal end of the silicone body 111 to the distal end of the silicone body 111. In this way, support force of the stent body 110 can be effectively improved by the mesh frame 112. Compared with an existing silicone stent 100 in which support force of a stent body 110 is merely provided by a silicone body 111, support force that needs to be provided by the silicone body 111 in the silicone stent 100 of this embodiment is relatively small. In this case, a wall thickness of the silicone body 111 can be greatly reduced, and a wall thickness of the formed stent body 110 is also greatly reduced. In this way, while being implanted, the silicone stent 100 can be put into the delivery device 200 and can be implanted under the side view of the flexible bronchoscope in the conventional OTW manner. This is helpful to reduce difficulties in implantation and surgery, and thus a learning curve of an implantation operation can be effectively shortened.

It should be noted that, in the description of this embodiment, a "proximal end" of a component refers to an end that is of the component and that is close to an outer side of a human body after the component is implanted in the human body. Correspondingly, a "distal end" refers to an end opposite to the "proximal end". In other words, the "distal end" refers to an end that is of the component and that is close to an inner side of the human body after the component is implanted in the human body. In this embodiment, the stent body 110 is in a cylindrical shape. After being implanted, the stent body 110 extends along the human trachea. A proximal end and a distal end of the stent body 110 are two ends of the stent body 110 along the axial direction of the stent body 110.

It should also be noted that, in the description of this embodiment, that "the mesh frame 112 circumferentially covers the silicone body 111" should be broadly explained. It may be understood as that the mesh frame 112 is located on an inner side of the silicone body 111, and the mesh frame 112 covers an inner wall of the silicone body 111; or it may be understood as that the mesh frame 112 is located on an outer side of the silicone body 111, and the mesh frame 112 covers an outer wall of the silicone body 111; or it may be understood as that the mesh frame 112 covers the silicone body 111 from the internal, that is, in this case, the mesh frame 112 is located within the silicone body 111, and a circumferential direction of the mesh frame 112 extends along a circumferential direction of the silicone body 111. In other words, the mesh frame 112 is approximately a meshed cylinder with an inner diameter larger than an inner diameter of the silicone body 111 and with an outer diameter smaller than an outer diameter of the silicone body 111.

The silicone stent 100 provided in this embodiment is further described below.

Figure 4:
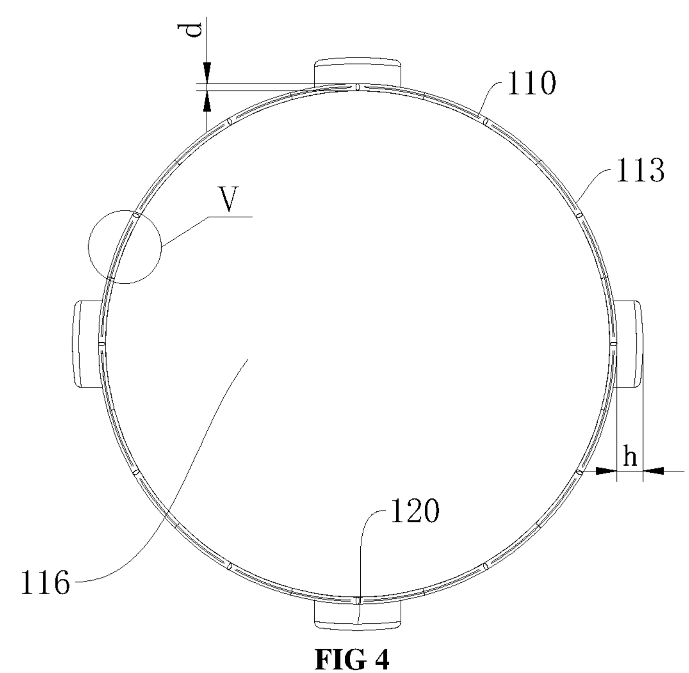
FIG. 4 is a schematic structural diagram of a silicone stent in a second visual angle according to an embodiment of this disclosure.
Figure 5:
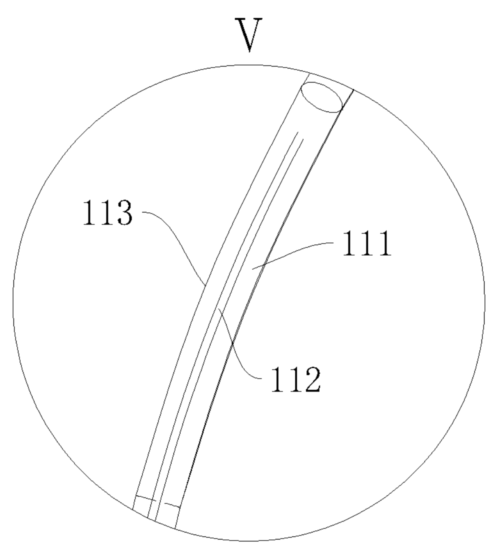
FIG. 5 is an enlarged schematic diagram of a partial structure at position V in FIG. 4.
Figure 6:
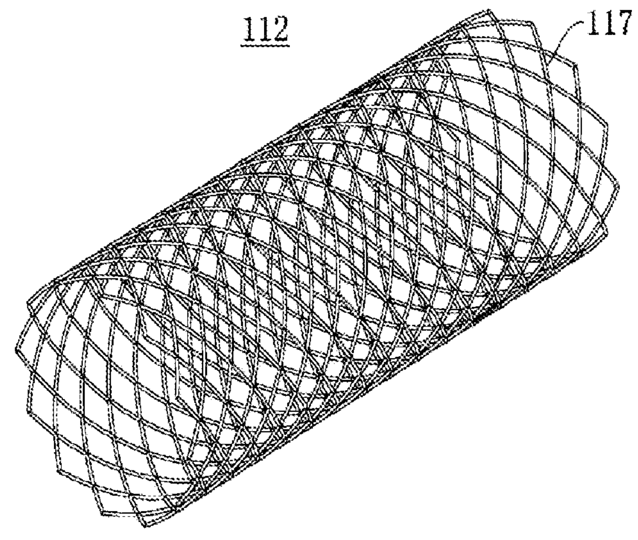
FIG. 6 is a schematic structural diagram of a mesh frame in a silicone stent according to an embodiment of this disclosure.

FIG. 4 is a schematic structural diagram of a silicone stent 100 in a second visual angle according to an embodiment. FIG. 5 is an enlarged schematic diagram of a partial structure at position V in FIG. 4. FIG. 6 is a schematic structural diagram of a mesh frame 112 in a silicone stent 100 according to an embodiment. Referring to FIG. 1, FIG. 4, FIG. 5, and FIG. 6, in this embodiment, the mesh frame 112 is in a cylindrical shape, and the silicone body 111 is molded on the mesh frame 112, to form the stem body 110 of the silicone stent 100. Correspondingly, the silicone body 111 is in a cylindrical shape that is similar to the shape of the mesh frame 112, so that the circumferentially sealed space 116 is defined within the silicone body 111. Meanwhile, the distal end and the proximal end of the silicone body 111 are respectively provided with the distal-end opening 115 and the proximal-end opening 114 that communicate with the space 116. In this way, after the silicone stent 100 is implanted into the human trachea, the trachea is pushed to open through abutting between the silicone stent 100 and a wall surface of the human trachea. In addition, the space 116 formed in the silicone body 111 can make the trachea unobstructed. Meanwhile, the stent body 110 is also in a cylindrical shape that is similar to the shape of the mesh frame 112.

Specifically, the mesh frame 112 is of an integral structure in a meshed cylindrical shape that is braided by a metal wire 117. In other words, the mesh frame 112 extends from the proximal end of the silicone body 111 to the distal end of the silicone body 111. Optionally, the mesh frame 112 is braided by using one metal wire 117. Optionally, the metal wire 117 is a nickel-titanium alloy metal wire.

Optionally, the silicone body 111 is molded on the mesh frame 112 by means of film coating. Specifically, liquid silicone is attached on the mesh frame 112, and the silicone body 111 is formed after the liquid silicone is solidified. The silicone body 111 is entirely wrapped on the mesh frame 112, and the silicone body 111 seals each grid of the mesh frame 112, so that the circumferentially sealed space 116 of which two axial ends respectively communicate with the exterior through the proximal-end opening 114 and the distal-end opening 115 is formed within the silicone body 111. In other words, in this case, the mesh frame 112 is located within the silicone body 111 (as shown in FIG. 5). Molding the silicone body 111 on the mesh frame 112 by means of film coating can not only ensure connection reliability between the silicone body 111 and the mesh frame 112, but is also helpful to make ensure that the manufactured stent body 110 has a sufficiently small thickness. In this way, the silicone stent 100 can be implemented more successfully in an OTW manner.

It should be noted that, the manner of manufacturing the silicone body 111 is not limited herein. It can be understood that in other embodiments, other manners can also be used, such as coating a periphery of the mesh frame 112 with sheet-like silicone to form the silicone body 111.

Referring to FIG. 4, optionally, the wall thickness d of the stent body 110 satisfies 0.05 mm≤d≤0.8 mm Specifically, the wall thickness of the stent body 110 is a distance between an inner peripheral wall and an outer peripheral wall 113 of the stent body 110. Since the silicone body 111 is molded on the mesh frame 112 by means of film coating, an outer peripheral wall and an inner peripheral wall of the molded silicone body 111 can be considered as the outer peripheral wall 113 and the inner peripheral wall of the stent body 110.

In this embodiment, it is satisfied that 0.1 mm≤d≤0.6 mm. Optionally, d=0.1 mm, 0.2 mm, 0.3 mm, 0.4 mm, 0.5 mm, or 0.6 mm. It can be understood that in other embodiments, the wall thickness of the stent body 110 can also be specifically set. For example, the wall thickness is set to be 0.05 mm, 0.7 mm, or 0.8 mm.

Referring to FIG. 1 and FIG. 4, in this embodiment, the outer peripheral wall 113 of the stent body 110 is provided with a plurality of protrusions 120 in a protruding manner. By providing a plurality of protrusions 120 that protrude from the outer peripheral wall 113 of the stent body 110, after the silicone stent 100 is implanted into the human trachea, the protrusion 120 abuts against the wall surface of the trachea. Displacement of the silicone stent 100 can be effectively avoided through the abutting between the protrusion 120 and the trachea.

Optionally, the protrusion 120 is in a column shape. When the protrusion 120 abuts against the wall surface of the trachea, a portion of a wall surface of the outer peripheral wall 113 of the stent body 110 is separated from the wall surface of the trachea. In this case, a gap is formed between an outer peripheral wall of the stent body 110 and the wall surface of the trachea. When the silicone stent 100 is supported in the trachea, cilia on a surface of the trachea swings back and forth to transmit a secretion or a sputum in the trachea to outside of the body. In this way, a mucus clearing function of the cilium in the trachea is remained, and tension of an air-fluid level of a mucous membrane in the trachea is ensured. Specifically, the protrusion 120 protrudes outward along a radial direction of the stent frame 110. Optionally, the protrusion 120 is in a cylindrical shape.

It should be noted that in this embodiment, to enable the cilium in the trachea to remain the mucus clearing function after the silicone stent 100 is implanted in the human trachea, the protrusion 120 is set to a column shape. It can be understood that in other embodiments, the shape of the protrusion 120 may also be set according to requirements. For example, the protrusion 120 is set to an annular shape.

Optionally, a thickness h of the protrusion 120 satisfies 0.5 mm≤h≤4 mm. It should be noted that, the thickness h of the protrusion 120 is a height for which the protrusion 120 protrudes out of the outer peripheral wall 113 of the stent body 110. In other words, the thickness h of the protrusion 120 is a distance from an end surface of an end that is of the protrusion 120 and that is away from the outer peripheral wall 113 of the stent body 110 to the outer peripheral wall 113 (as shown in FIG. 4). Optionally, h=0.5 mm, 1 mm, 2 mm, 3 mm, or 4 mm.

Optionally, the plurality of protrusions 120 include a plurality of columns of protrusions 120 that are uniformly distributed along a circumferential direction of the stent body 110, and each column of protrusions 120 include a plurality of protrusions 120 disposed at intervals along the axial direction of the stent body 110.

Figure 7:
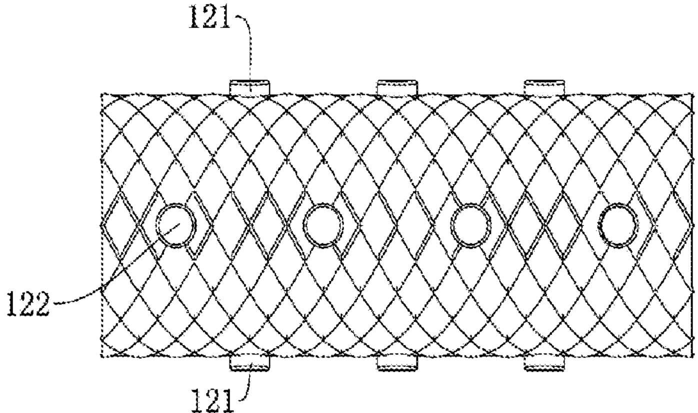
FIG. 7 is a schematic structural diagram of a silicone stent in a third visual angle according to an embodiment of this disclosure.

FIG. 7 is a schematic structural diagram of a silicone stent 100 in a third visual angle according to an embodiment of this disclosure. Referring to FIG. 1, FIG. 4, and FIG. 7, optionally, a plurality of protrusions 120 in two adjacent columns of protrusions 120 are alternately disposed along the axial direction of the stent body 110. Specifically, the two adjacent columns of protrusions 120 are a first column and a second column A plurality of protrusions 120 in the first column are the first protrusions 121, and a plurality of protrusions 120 in the second column are the second protrusions 122. The first protrusions 121 and the second protrusions 122 are alternately disposed along the axial direction of the stent body 110. The first protrusions 121 and the second protrusions 122 are alternately disposed along the axial direction of the stent body 110. Therefore, the first protrusions 121 and the second protrusions 122 are disposed in a staggered way in an axial direction of the trachea to support the wall surface of the trachea. In this way, the wall surface of the trachea can be better stretched to be separated from the outer peripheral wall 113 of the stent body 110, and the cilium in the trachea has a better mucus clearing effect.

It should be noted that a manner of disposing the protrusions 120 are not limited herein. It can be understood that in other embodiments, the protrusions 120 can also be disposed in other ways as required. For example, the plurality of protrusions 120 are spirally disposed, around an axis of the stent body 110, on the outer peripheral wall 113 of the stent body 110, or the plurality of protrusions 120 are dispersedly disposed on the outer peripheral wall 113 of the stent body 110.

In this embodiment, the protrusion 120 is bonded and fixed on the stent body 110. Specifically, after the silicone body 111 is molded on the mesh frame 112 by means of film coating, the pre-manufactured protrusion 120 is bonded and fixed on the outer peripheral wall 113 of the stent body 110. Optionally, to ensure connection reliability between the protrusion 120 and the stent body 110, the bonding operation is performed for the protrusions 120 after film coating is performed on the mesh frame 112 to mold the silicone body 111 on the mesh frame 112. The silicone stent 100 is vulcanized after the bonding operation. It can be understood that in other embodiments, a molding manner of the protrusion 120 can also be set according to requirements. For example, the protrusion 120 that protrudes from the outer peripheral wall 113 of the stent body 110 is formed in a manner that the protrusion 120 is integrally formed with the silicone body 111. Moreover, the silicone stent 100 manufactured in this way can be placed in a delivery device 200 with an outer diameter less than Φ 8 mm. Certainly, the silicon stent 100 can also be placed in a delivery device 200 with another outer diameter, which is not limited to a delivery device 200 with an outer diameter of Φ 8 mm.

It should be noted that, the manner of manufacturing the protrusion 120 is not limited herein. It can be understood that in other embodiments, the protrusion 120 can also be formed in other manners. For example, a protruding portion that protrudes from the outer peripheral wall of the mesh frame 112 is disposed on the mesh frame 112. In this way, when the mesh frame 112 is performed with film coating, a part of liquid silicone is attached at the protruding portion, to form the protrusion 120.

Specifically, in the silicone stent 100, the mesh frame 112 can be considered as a protruding portion that includes a cylindrical cylinder and that is disposed to protrude from an outer wall of the cylinder. During molding, the liquid silicone is attached at the cylinder, to form the silicone body 111. Optionally, the protruding portion and the cylinder are integrally braided by using one metal wire 117. By disposing the protruding portion on the mesh frame 112 to naturally form the protrusion 120 at the protruding portion during film coating, not only a production process is simplified, but also a manufacturing process is simplified. The protruding portion is manufactured by using the metal wire 117, so that support force of the protrusion 120 can be effectively enhanced by the protruding portion. In this way, the wall surface of the trachea can be better stretched to be separated from the outer peripheral wall 113 of the stent body 110. This also helps to reduce a size of the silicone stent 100 when the silicone stent 100 is in a contracted state, so that the silicone stent 100 can be placed in a delivery device 200 with a smaller specification, being more convenient and simpler to be implanted. Moreover, the silicone stent 100 manufactured in this way can be placed in a delivery device 200 with an outer diameter less than Φ 6 mm. Certainly, the silicon stent 100 can also be placed in a delivery device 200 with another outer diameter, for example, the delivery device 200 with the outer diameter of Φ 8 mm.

Regarding the silicone stent 100 provided in this embodiment, the working principle of the silicone stent 100 is as follows.

During use, the silicone stent 100 is compressed to be in a contracted state and is placed in the accommodation cavity 214 of the delivery device 200. A distal end of the delivery device 200 enters the human trachea along a guide wire, and then the silicone stent 100 is released under the side view of the flexible bronchoscope. During releasing, the delivery device 200 is operated to push the silicone stent 100 out of the accommodation cavity 214 of the delivery device 200. After leaving the accommodation cavity 214, the silicone stent 100 expands to a state shown in FIG. 1. The silicone stent 100 stretches the trachea to ensure that the trachea is unobstructed.

The silicone stent 100 provided in this embodiment at least has the following advantages.

Regarding the silicone stent 100 provided in this embodiment, by disposing the mesh frame 112 in the silicone body 111, the support force of the silicone stent 100 comes from the mesh frame 112 and the silicone body 111. In this way, it can be ensured that when a thickness of the stent body 110 of the silicone stent 100 is relatively small, the silicone stent 100 can still have sufficient support force. Thus, the silicone stent 100 can be placed in the accommodation cavity 214 of the delivery device 200, and can be implanted in an OTW manner, without using a rigid bronchoscope. As a result, the implantation operation is simpler, so that difficulties in surgery are reduced and a lot of operation time is saved. Meanwhile, through disposing of the protrusion 120, position stability of the silicone stent 100 in the trachea is high, and the mucus clearing function of some cilia is remained. This helps to clear secretions around the silicone stent, bringing in a better use effect.

Figure 8:
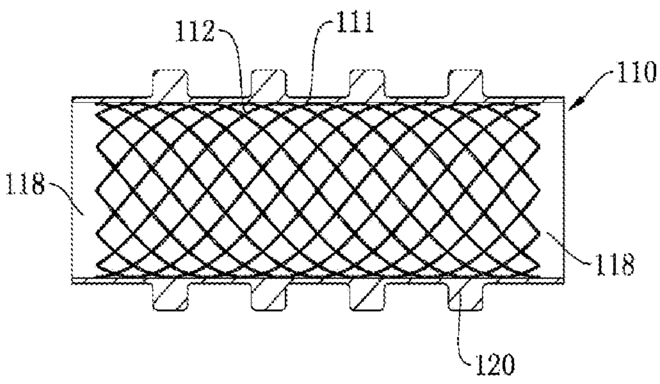
FIG. 8 is a schematic cross-sectional structural diagram of another silicone stent according to an embodiment of this disclosure.

FIG. 8 is a schematic cross-sectional structural diagram of another silicone stent 100 according to an embodiment. Referring to FIG. 8, this embodiment further provides another silicone stent 100. The silicone stent 100 is approximately the same as the silicone stent 100 shown in FIG. 1. A difference is that relative positions of a silicone body 111 and a mesh frame 112 are different. Specifically, the silicone body 111 is fixed at a periphery of the mesh frame 112.

Optionally, the stent body 110 further includes skirt edges 118 connected at two ends of the silicone body 111. Along an axial direction of the silicone stent 100, the skirt edges 118 are located on two sides of the mesh frame. Specifically, the skirt edges 118 located at two ends of the silicone body 111 respectively are a first skirt edge and a second skirt edge. The first skirt edge is fixedly connected to a proximal end of the silicone body 111, so that a proximal end of the mesh frame 112 is covered by the first skirt edge, thereby preventing the mesh frame 112 from stimulating human tissue after the silicone stent 100 is implanted into a human body.

An axial size l of the skirt edge 118 satisfies 0≤l≤6 mm. Optionally, l=1 mm, 4 mm, 5 mm, or 6 mm. Preferably, it is satisfied that 2 mm≤l≤3 mm. Optionally, l=2 mm, 2.5 mm, or 3 mm.

Optionally, the silicone body 111 is integrally formed with the skirt edge 118. Specifically, a length of a silicone cylinder is greater than that of the mesh frame 112. In this way, when the mesh frame 112 is bonded and fixed on an inner peripheral wall of the silicone cylinder, both ends of the silicone cylinder are disposed to protrude from the mesh frame 112. In other words, end surfaces of two ends of the silicone cylinder are respectively located on two sides of the mesh frame 112 in an axial direction. In this way, the first skirt edge and the second skirt edge are respectively formed on two sides of the mesh frame 112 in the axial direction. A portion that is of the silicone cylinder and that is between the first skirt edge and the second skirt edge forms the silicone body 111. In other words, the silicone cylinder can be considered as a cylindrical structure integrally formed by the silicone body 111, the first skirt edge, and the second skirt edge. Optionally, a protrusion 120 is integrally molded on the outer peripheral wall of the silicone cylinder. Specifically, during production, the silicone cylinder whose outer peripheral wall is provided with the protrusion 120 is integrally formed by solidifying liquid silicone. It can be understood that in other embodiments, the protrusion 120 can also be bonded and fixed on the outer peripheral wall of the silicone cylinder in a bonding manner.

During production, the silicone cylinder whose outer peripheral wall is provided with the protrusion 120 is pre-manufactured. For manufacturing of the silicone cylinder, reference can be made to an existing method for manufacturing a silicone stent. Subsequently, a small amount of liquid silicone is coated on the mesh frame 112, and the silicone cylinder is sleeved outside the mesh frame 112 for vulcanization, to fix the mesh frame 112 and the silicone cylinder. In this way, the stent body 110 with skirt edges 118 at both ends is manufactured. Optionally, the liquid silicone is coated on both ends of the mesh frame 112 in the axial direction. In this way, after vulcanization, both ends of the mesh frame 112 in the axial direction are bonded and fixed to the silicone cylinder at the same time.

It should be noted that, the mesh frame 112 connected to the inner peripheral wall of the silicone cylinder is a bare frame. It can be understood that in other embodiments, a silicon layer (not shown in the figure) can be pre-wrapped on the mesh frame 112 as required, and then the silicon layer is fixedly connected to the silicon cylinder, to fixedly connect the mesh frame 112 to the silicon body 111 through the fixed connection between the silicon layer and the silicon cylinder. Specifically, the silicone cylinder is sleeved on the mesh frame 112 wrapped with the silicone layer. Since the silicone cylinder and the silicone layer are both made of silicone, the silicone cylinder and the silicone layer may be bonded into one piece by vulcanizing the silicone cylinder and the mesh frame 112 wrapped with the silicone layer. Since the mesh frame 112 is wrapped with the silicon layer, compared with a manner of directly fixing the bare frame on an inner wall of the silicon cylinder, requirements on support force of the silicon stent 100 can be satisfied by using a silicon cylinder with a smaller thickness.

This embodiment also provides an implantation system. The implantation system includes a delivery device 200 and the silicone stent 100 described above.

A structure of the delivery device 200 is shown in FIG. 2 and FIG. 3. Specifically, the delivery device 200 includes an inner tube 211, a middle tube 212, an outer tube 213, a proximal-end handle 216, and a distal-end handle 217. The inner tube 211, the middle tube 212, and the outer tube 213 are sleeved successively. To be specific, the inner tube 211 is located on an innermost side, and the outer tube 213 is located on an outermost side. The inner tube 211 is fixedly connected to the middle tube 212, the middle tube 212 is fixedly connected to the proximal-end handle 216, and the outer tube 213 is fixedly connected to the distal-end handle 217. When the middle tube 212 is located on a side that is of an end surface of a distal end of the outer tube 213 and that is close to a proximal end, an accommodation cavity 214 located on a side that is of an end surface of a distal end of the middle tube 212 and that is close to the distal end is formed between the outer tube 213 and the inner tube 211. In other words, the accommodation cavity 214 can basically be considered to be located at a distal end of the delivery device 200.

During use, the silicone stent 100 is mounted in the accommodation cavity 214 in a contracted state, and it is ensured that the entire silicone stent 100 enters the accommodation cavity 214. Subsequently, under guide of a guide wire, the distal end of the delivery device 200 extends into a human trachea, until a preset position is reached, and then the proximal-end handle 216 is pushed to approach the distal-end handle 217. Correspondingly, the middle tube 212 moves towards the interior of the human body relative to the outer tube 213, and the silicon stent 100 in the accommodation cavity 214 protrudes out of the accommodation cavity 214 under push of the middle tube 212. A limiting function of the outer tube 213 on the silicone stent 100 is eliminated after the silicone stent 100 extends out of the accommodation cavity 214. The silicone stent 100 expands to stretch the trachea, thereby completing implantation of the silicone stent 100. Meanwhile, the implantation process can be observed under side view of a flexible bronchoscope, thereby ensuring an implantation effect and reducing difficulties in implantation.

Optionally, the distal end of the middle tube 212 is further provided with a developing ring 215. The end surface of the distal end of the middle tube 212 described above is an end surface of a distal end of the developing ring 215. Specifically, the developing ring 215 is fixedly connected to the middle tube 212 by means of adhesive bonding.

This embodiment also provides a manufacturing for manufacturing a silicone stent 100.

Specifically, the manufacturing method includes:

molding a silicone body 111 on a cylindrical mesh frame 112, so that a circumferentially sealed space 116 is defined within the silicone body 111. A distal end and a proximal end of the silicone body 111 are respectively provided with a proximal-end opening 114 and a distal-end opening 115 that communicate with the space 116. The mesh frame 112 circumferentially covers the silicone body 111 and runs in an axial direction of the silicone body 111. The mesh frame 112 extends from the proximal end of the silicone body 111 to the distal end of the silicone body 111. In other words, the manufacturing method provided in this embodiment can be used for manufacturing the silicone stent 100 described above.

The step of molding the silicone body 111 on the cylindrical mesh frame 112 includes:

coating the mesh frame 112 with silicone to mold the silicone body 111 on the mesh frame 112, wherein the mesh frame 112 and the silicone body 111 attached on the mesh frame 112 form a stent body 110 of the silicone stent 100; and bonding a pre-manufactured protrusion 120 to an outer wall of the stent body 110 to obtain the silicone stent 100.

Specifically, to ensure bonding reliability between the protrusion 120 and the stent body 110, the silicone stent 100 is obtained after the silicone body 111 is molded through film coating silicone on the mesh frame 112, that is, the pre-manufactured protrusion 120 is bonded to an outer peripheral wall 113 of the stent body 110 to form the silicone stent 100. Finally, the entire silicone stent 100 is vulcanized. It can be understood that in other embodiments, the fixing mode between the protrusion 120 and stent body 110 can be specifically set as required.

Optionally, a step of manufacturing the protrusion 120 is further included before the step of bonding the protrusion 120 to the outer peripheral wall 113 of the stent body 110. Specifically, the protrusion 120 is molded by stamping sheet-like silicone.

Optionally, a step of braiding the mesh frame 112 is further included before the step of molding the silicone body 111 on the cylindrical mesh frame 112. Specifically, the cylindrical mesh frame 112 is formed by winding a single metal wire 117 spirally around a preset axis. The preset axis is an axis of the mesh frame 112, and the manufactured mesh frame 112 has rhombus grids.

It should be noted that in this embodiment, the silicone stent 100 is formed by first manufacturing the stent body 110 and then performing bonding on the stent body 110. It can be understood that in other embodiments, the silicone stent 100 can also be formed in other ways.

For example, the step of molding the silicone body 111 on the cylindrical mesh frame 112 includes: film coating the mesh frame 112 with silicone to mold the silicone body 111 on the mesh frame 112. The mesh frame 112 has a protruding portion disposed on an outer wall surface of the mesh frame 112. During the process of performing film coating on the mesh frame 112, the protruding portion is performed with film coating together with the mesh frame 112, and the protrusion 120 is film coated with silicone to form the protrusion 120 of the silicone stent 100. In other words, the stent body 110 of the silicone stent 100 is molded simultaneously with the protrusion 120 in one step. Optionally, the protrusion 120 and the mesh frame 112 are integrally braided with a single metal wire 117. Specifically, in the process of braiding the mesh frame 112 with the metal wire 117, the metal wire 117 is bent to a radial outer side of the mesh frame 112 at a preset position, to form the protruding portion.

Alternatively, the mesh frame 112 may also be performed with film coating to form the mesh frame 112 having the silicone body 111. The protrusion 120 is integrally formed on an outer peripheral wall of the silicone body 111. Specifically, the step of molding the silicone body 111 on the cylindrical mesh frame 112 includes the following steps.

A) Placing the mesh frame 112 in a mold. The mold has a molding cavity for molding the silicone stent 100, and the molding cavity has an inner peripheral surface corresponding to the outer wall surface of the mesh frame 112. Meanwhile, a recess is disposed on the inner peripheral surface. Specifically, the recess is a column-shaped recess formed by means that the inner peripheral surface is depressed outwards in a radial direction.

B) Injecting liquid silicone into the mold, and filling the recess on an inner peripheral surface of the mold with the liquid silicone. The liquid silicone is wrapped on the mesh frame 112, so that the cooled liquid silicone forms the silicone body 111 on the mesh frame 112. Moreover, a portion at which the recess is filled with the liquid silicone forms the protrusion 120. In other words, an outer wall of the silicone body 111 has the protrusion 120 corresponding to the recess, and the protrusion 120 is integrally formed with the silicone body 111.

Alternatively, the silicone body 111 may be molded on the mesh frame 112 in a bonding manner.

Optionally, the step of molding the silicone body 111 on the mesh frame 112 includes:

respectively bonding and fixing a proximal end and a distal end of the mesh frame 112 on an inner peripheral wall of a silicone cylinder. A portion that is of the silicone cylinder and that is located between the proximal end and the distal end of the mesh frame 112 forms the silicone body 111. Portions, at two ends in an axial direction of the silicone cylinder, that protrude out of the mesh frame 112 form skirt edges 118, so that an end portion of the mesh frame 112 is covered by the skirt edge 118. In this way, the mesh frame 112 is prevented from stimulating human tissue when the human tissue grows and enters the silicone stent 100. It can be understood that in other embodiments, when the silicone body 111 is molded on the mesh frame 112 by means of film coating, skirt edges 118 may also be disposed at both ends of the silicone body 111, to prevent the mesh frame 112 from stimulating the human tissue.

Specifically, liquid silicone is respectively coated on the proximal end and the distal end of the mesh frame 112, and then the silicone cylinder is sleeved on the mesh frame 112 for vulcanization, to fix the proximal end and the distal end of the mesh frame 112 on the silicone cylinder by the liquid silicone. The silicone cylinder forming the silicone body 111 is manufactured separately from the mesh frame 112, and a length of the silicone cylinder is greater than that of the mesh frame 112. Therefore, silicon cylinders of a same specification can be adapted to mesh frames 112 of different length specifications, thereby helping to reduce production costs.

Optionally, the protrusion 120 is integrally formed on an outer peripheral wall of the silicone cylinder. Optionally, a step of braiding the mesh frame 112 is further included before the step of molding the silicone body 111 on the mesh frame 112. Optionally, a step of manufacturing the silicone cylinder is further included before the step of molding the silicone body 111 on the mesh frame 112.

It should be noted that the mesh frame 112 bonded in the silicone cylinder is a bare frame. It can be understood that in other embodiments, the mesh frame 112 can also be performed with film coating in advance to form a silicone layer wrapping the mesh frame 112 on the mesh frame 112. Subsequently, the mesh frame 112 performed with film coating is bonded and fixed in the silicone cylinder. Specifically, the step of molding the silicone body 111 on the mesh frame 112 includes:

sleeving the silicone cylinder on the mesh frame 112 wrapped with the silicone layer (not shown in the figures); and vulcanizing the silicone cylinder and the mesh frame 112 wrapped with the silicone layer, so that the silicone cylinder is bonded and fixed to the silicone layer. In this case, the portion that is of the silicone cylinder and that is located between the proximal end and the distal end of the mesh frame 112 forms the silicone body 111, and two ends in the axial direction of the silicone cylinder protrude out of the mesh frame 112 to form the skirt edges 118.

The descriptions above are merely specific embodiments of this disclosure, but the protection scope of this disclosure is not limited thereto. Any change or replacement that can be readily figured out by a person skilled in the art within the technical scope of this disclosure shall fall within the protection scope of this disclosure. Therefore, the protection scope of this disclosure shall be subject to the protection scope of the claims.

INDUSTRIAL APPLICABILITY

The silicone stent provided in this disclosure includes the stent body. The stent body includes the mesh frame and the silicone body molded on the mesh frame. The circumferentially sealed space is defined within the silicone body, and the distal end and the proximal end of the silicone body are respectively provided with the distal-end opening and the proximal-end opening that communicate with the space. During use, the silicone stent is implanted into the human trachea, and the space defined within the silicone body communicates with the trachea, thereby ensuring that the trachea is unobstructed. Because the stent body of the silicone stent is formed through the mesh frame and the silicone body together, and the mesh frame circumferentially covers the silicone body, along the axial direction, the mesh frame extends from the proximal end of the silicone body to the distal end of the silicone body. In this way, compared with the existing silicone stent in which the support force of the stent body is merely provided by the silicone body, the support force of the stent body can be effectively improved by using the mesh frame. Therefore, the silicone stent provided in this disclosure can greatly reduce the wall thickness of the silicone body. Moreover, the wall thickness of the formed stent body is also greatly reduced. In this way, while being implanted, the silicone stent can be put into the delivery device, and can be implanted by using the delivery device under the side view of the flexible bronchoscope in the conventional OTW manner. This is helpful to reduce the difficulties in implantation and surgery, and thus the learning curve of the implantation operation can be effectively shortened. According to the implantation system provided in this disclosure, the silicone stent can be implanted into the human trachea by using the delivery device in the conventional OTW manner. Therefore, the implantation system has the following beneficial effects of the silicone stent: difficulties in implantation and surgery are low and the learning curve of the implantation operation is short. The manufacturing method provided in this disclosure can be used to manufacture the silicone stent described above. Therefore, the manufactured silicone stent also has the beneficial effects of low difficulties in implantation and surgery and a short learning curve of the implantation operation.

What is claimed is:

1. A silicone stent for trachea, comprising a stent body, wherein the stent body comprises a braided mesh frame and a silicone body molded on the braided mesh frame; a circumferentially sealed space is defined within the silicone body; a distal end and a proximal end of the silicone body respectively have a distal-end opening and a proximal-end opening that communicate with the space; wherein an inner diameter of the circumferentially sealed space, an inner diameter of the distal-end opening, and an inner diameter of the proximal-end opening are substantially the same; wherein the silicone body is molded on the braided mesh frame by film coating; and the braided mesh frame extends from the proximal end of the silicone body to the distal end of the silicone body, wherein the stent body further comprises skirt edges connected at two ends of the silicone body; and along an axial direction of the silicone stent, the skirt edges are located on two sides of the braided mesh frame, with an axial size L of the skirt edge satisfying 0≤L≤6 mm, wherein the silicone stent is configured to be received in an accommodation cavity of a delivery device in a contracted state, and to be released and implanted, under guide of a guide wire and under a side view of the flexible bronchoscope, in the trachea by the delivery device;

wherein an outer peripheral wall of the stent body is provided with a plurality of protrusions, wherein the protrusions are so configured that when the silicone stent is implanted into the human trachea, the protrusions abut against an inner wall surface of the trachea, such that an outer peripheral surface of the stent body is separated from the inner wall surface of the trachea, so as to form a gap between the outer peripheral surface of the stent body and the inner wall surface of the trachea, wherein the plurality of protrusions comprise a plurality of columns of protrusions that are uniformly distributed along a circumferential direction of the stent body, and each column of protrusions comprise a plurality of protrusions disposed at intervals along an axial direction of the stent body, wherein protrusions in two adjacent columns of protrusions are alternately disposed along the axial direction of the stent body, wherein a thickness (h) of the protrusions satisfies 0.5 mm≤h≤4 mm.

2. The silicone stent according to claim 1, wherein the protrusion is integrally formed with the silicone body.

3. The silicone stent according to claim 1, wherein the braided mesh frame has a protruding portion, and the protruding portion is film coated to form the protrusion.

4. The silicone stent according to claim 1, wherein a plurality of protrusions in each column of protrusions are spirally distributed around an axis of the stent body; or a plurality of protrusions are distributed dispersedly.

5. The silicone stent according to claim 1, wherein a wall thickness (d) of the stent body satisfies 0.05 mm≤d≤0.8 mm.

6. The silicone stent according to claim 1, wherein the skirt edge is integrally formed with the silicone body.

7. An implantation system, comprising a delivery device and the silicone stent according to claim 1, wherein the delivery device has an accommodation cavity, and the silicone stent is accommodated in the accommodation cavity in a contracted state, so that the silicone stent is released and implanted, under guide of a guide wire and under a side view of the flexible bronchoscope, in the trachea by the delivery device.

* * * * *